United States Patent [19]

Heine et al.

[11] 4,273,112
[45] Jun. 16, 1981

[54] LARYNGOSCOPE

[75] Inventors: Helmut A. Heine, Herrsching; Helmut W. Rosenbusch, Weilheim; Rudolf Kratzer, Oberalting, all of Fed. Rep. of Germany

[73] Assignees: Propper Manufacturing Co., Inc., Long Island City, N.Y.; Heine Optotechnik GmbH & Co. KG, Herrsching, Fed. Rep. of Germany

[21] Appl. No.: 932,494

[22] Filed: Aug. 10, 1978

[30] Foreign Application Priority Data

Aug. 24, 1977 [DE] Fed. Rep. of Germany ....... 2738202

[51] Int. Cl.³ ............................................. A61D 1/06
[52] U.S. Cl. ..................................... 128/11; 128/16; 362/32
[58] Field of Search ....................................... 128/3–11, 128/15, 16, 18, 22, 23; 362/184, 188, 203, 207, 197, 199, 226, 448, 804, 32

[56] References Cited

U.S. PATENT DOCUMENTS

| 1,339,711 | 5/1920 | Park | 128/16 |
| 2,595,287 | 5/1952 | Perry | 362/226 |
| 3,384,076 | 5/1968 | Speelman | 128/9 |
| 3,579,269 | 5/1971 | Ostensen | 128/11 X |
| 3,638,644 | 2/1972 | Reick | 128/16 |
| 3,766,909 | 10/1973 | Ozbey | 128/11 |
| 3,916,881 | 11/1975 | Heine | 128/16 |
| 3,934,578 | 1/1976 | Heine | 128/9 |
| 4,086,919 | 5/1978 | Bullard | 128/11 |

Primary Examiner—Robert W. Michell
Assistant Examiner—Arthur S. Rose
Attorney, Agent, or Firm—Amster, Rothstein & Engelberg

[57] ABSTRACT

The invention relates to an improved laryngoscope with a mounting for the incandescent lamp which permits its easy removal for replacement purposes. In one embodiment the lamp can be removed upwardly from the handle of the laryngoscope and in other embodiments it can be removed downwardly with a battery housing located in the handle.

12 Claims, 6 Drawing Figures

LARYNGOSCOPE

The invention relates to a laryngoscope with a handle which contains an incandescent lamp and with a spatula which is pivotably attached to the handle and switches on the incandescent lamp when in its operating position.

Laryngoscopes are used to examine the larynx, the spatula being introduced into the trachea. The light which is required for the examination is conducted from the incadescent lamp to the point being observed via a light conductor mounted in the spatula in such a way that the point can be seen as clearly as possible.

One of the main fields of application for this type of laryngoscope is the introduction and attachment of the tracheal tube in the trachea during intubation narcosis. Laryngoscopes are used for the same purpose in artificial respiration. The spatula is shaped so that the tracheal tube can be introduced into the trachea without touching the patient. For this purpose, the spatula normally has an approximately U-shaped cross-section or has a rib which holds the sensitive parts of the patient's throat away from the main surface of the spatula and thus forms a free space through which the tracheal tube can be introduced.

Since laryngoscopes are always used in situations where life is at stake, frequently in the care of emergency cases, they must function reliably. One weak point is the incadescent lamp, failure of which can result in critical situations. It should therefore be possible to change the incandescent lamp as quickly as possible.

In the laryngoscope described in the introduction, which is known from U.S. Pat. No. 3,638,644, the incandescent lamp is screwed into a contact sleeve, which can be moved to and fro in the end part of the handle of the laryngoscope and which is pressed down, together with the incandescent lamp screwed into it, when the spatula is pivoted up into the operational position, so that the base contact of the incandescent lamp touches the contact pin of the battery arranged in the handle, thus connecting the incandescent lamp.

However, the contact sleeve is constructed in such a way that it can only be taken out of the handle after the screw cap which closes up the opposite end of the handle has been removed, together with the batteries. This process of removing the incandescent lamp is carried out relatively quickly, but it is extremely difficult to insert the incandescent lamp and the contact sleeve into the handle again. To do this, firstly the used incandescent lamp has to be unscrewed from the contact sleeve and a new incandescent lamp has to be screwed in. Then the incandescent lamp with the contact sleeve has to be passed through the handle with a special tool, for example a thin rod with its point covered over with a bicycle valve rubber, and threaded into the bore provided for it in the end part of the handle. Only then can the battery be inserted in the handle again and the handle closed up by means of the screw cap.

Changing the incandescent lamp in the known laryngoscope is therefore an exceedingly time-consuming process, and can seriously jeopardize the life of the patient.

The invention is therefore based on the task of producing a laryngoscope in which the incandescent lamp can be changed rapidly in an uncomplicated manner.

This task is solved in a first embodiment of the invention by mounting the contact sleeve in the end part of the handle so that it can be withdrawn outwards.

With the laryngoscope constructed according to the invention, the contact sleeve, together with the incandescent lamp, can be taken out and inserted again with a new incandescent lamp very quickly, and it is not necessary to screw the incandescent lamp into the contact sleeve. This only requires to be plugged into the latter.

In order to hold the contact sleeve as securely as possible in the handle, it is preferably mounted locked in the end part of the handle in such a way that the switching path towards the outside is restricted by the locking point.

Preferably, to facilitate withdrawal of the contact sleeve from the handle, a flange is provided on the end of the contact sleeve which projects beyond the end face of the handle.

According to a second embodiment of the invention, the contact sleeve is arranged in a battery unit provided in the handle and can be actuated by means of an actuating element which projects beyond the end face of the handle.

According to a third embodiment of the invention the incandescent lamp is arranged in a battery unit fitted in the handle, the actuating element acting on a contact which connects the handle housing to one of the contacts of the incandescent lamp when the actuating element is pressed down.

In the last embodiment of the invention to be described the incandescent lamp can be removed from the handle, together with the battery unit. The battery unit can be replaced very quickly by another with an incandescent lamp already screwed in, or the incandescent lamp in the battery unit can be changed and the latter inserted again in the handle. In this case as well, very little time is required to change the incandescent lamp.

The invention is described in greater detail in the following, with reference to the preferred construction examples shown in the drawings.

The laryngoscopes shown in FIGS. 1 to 6 all consist basically of a handle 10 and a spatula 14 which is pivoted on in the vicinity of one end face of the handle 10 by means of an axial pin 12. The axial pin 12 attached to the handle 10 lies in an open slot formed in the spatula 14 so that the spatula 14 can be taken off the handle 10. The spatula 14 is held on the axial pin 12 by means of a locking device which is not shown, so that it is secured to the handle and cannot slip off, but can be changed for another different-sized spatula 14 to suit the anatomical make-up of the patient.

Figure 1:
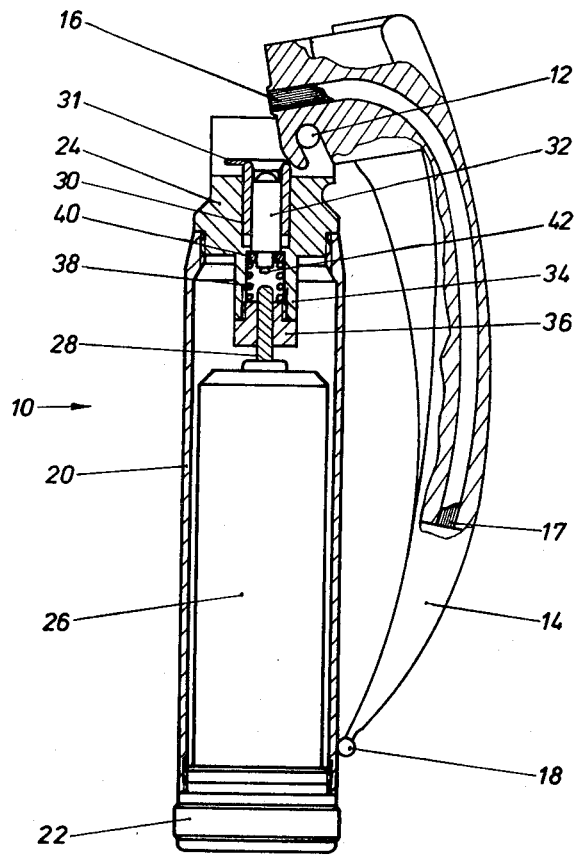
FIGS. 1, 3 and 5 show a partial section through three laryngoscopes according to the invention, with the spatula folded down in the rest position.
Figure 2:
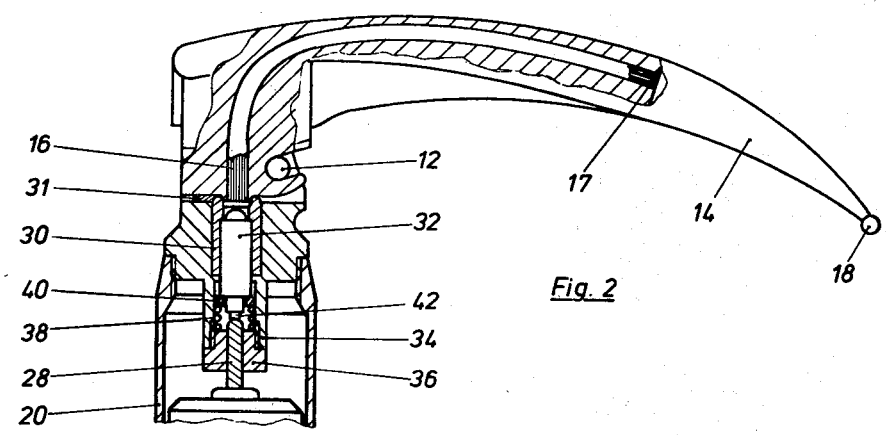
FIGS. 2, 4 and 6 show the partial section through the laryngoscopes shown respectively in the Figures listed above, with the spatula in the operational position.
Figure 3:
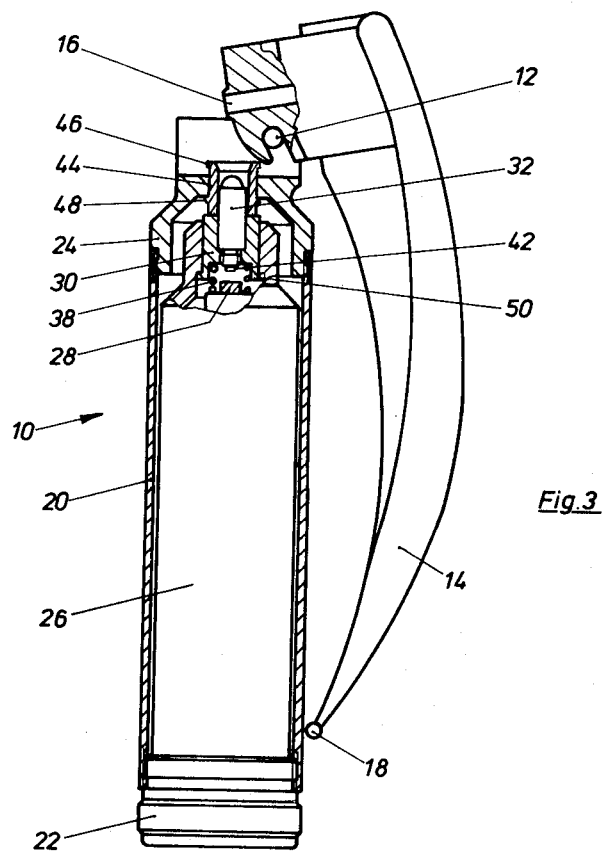
Figure 4:
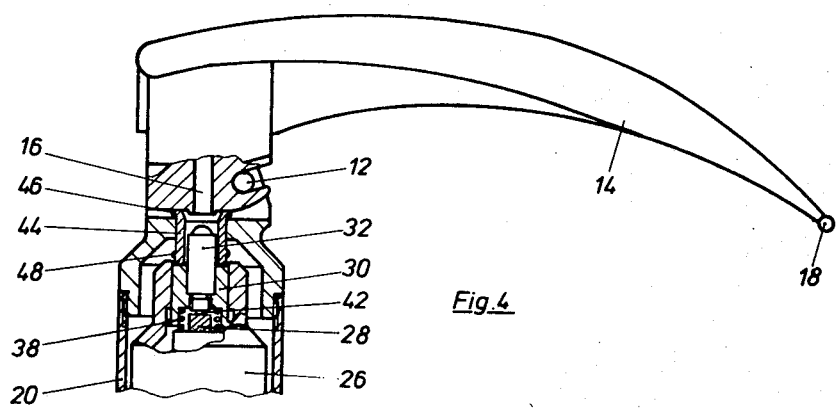
Figure 5:
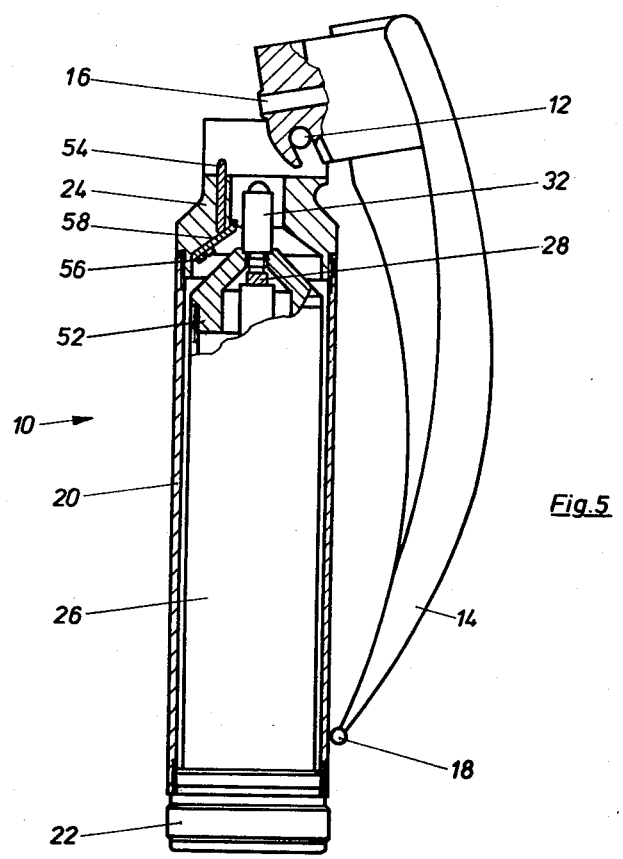
Figure 6:
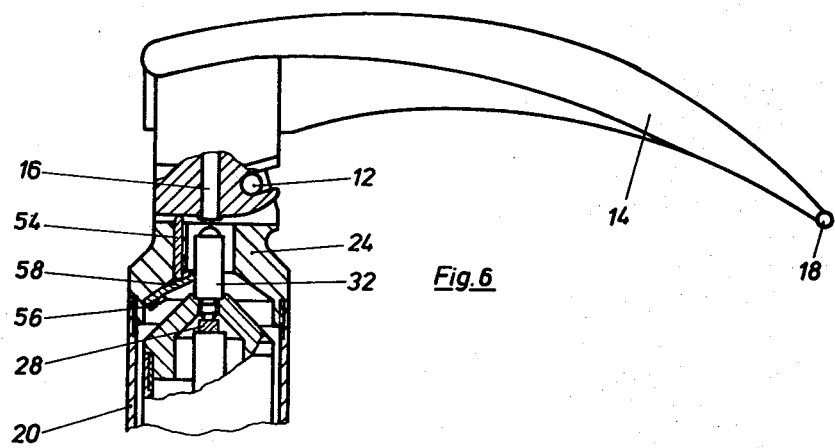

In addition, there is at least one further locking device, which is not shown, which holds the spatula in the operational position shown in FIGS. 2, 4 and 6. If required, a third locking device can be provided to hold the spatula in the rest position shown in FIGS. 1, 3 and 5.

A bunch 16 of light-conducting fibers runs through one of the side walls of the spatula 14 from the surface of the spatula 14 which terminates at the upper end face of the handle in the operational position, along approximately two-thirds of its total length in the direction of the tip of the spatula 14. The distal light outlet surface 17 of the bunch 16 of light-conducting fibers is shaped in such a way that the light falls on the object being observed, such as the epiglottis, for example, as effectively as possible.

At the front tip of the spatula 14 there is a bead 18. This serves mainly to prevent injury when the laryngoscope is inserted.

The handle 10 consists chiefly of a cylindrical housing 20, into the lower end of which, as shown in FIGS. 1, 3 and 5, a screw cap 22 is screwed. Into the opposite end, thus the upper end of the cylindrical housing 20, an attachment 24 is screwed. Inside the handle 10 there is a battery unit 26 with dry or chargeable batteries with a spring contact pin 28 projecting out of its upper end face.

In the embodiment shown in FIGS. 1 and 2, the attachment 24 has a central bore through it, in the upper section of which a contact sleeve 30 is inserted. At the upper end of the contact sleeve 30 an annular flange 31 is provided; this is cut back on the side facing the axial pin 12 in order to make room for the projection which engages round the axial pin 12. The contact sleeve 30 is inserted locked in the bore in the attachment 24 in such a way that it can be moved between the positions shown in FIGS. 1 and 2 after overcoming the locking point. The contact sleeve 30 holds an incandescent lamp 32, the socket of which rests at the top against a collar formed on the inner face of the contact sleeve 30.

A piece of tubing 34 is moulded onto the lower surface of the attachment 24, having its lower, open end closed by means of a screw cap 36. Against the inside of the end face of the screw cap 36 a helical spring 38 is braced, with its other end pressing the incandescent lamp 32 via a ring 40 which encircles the base contact 42 of the incandescent lamp 32 towards the collar formed on the internal face of the contact sleeve 30 and towards the locking device shown.

The contact pin 28 of the battery unit 26 projects through a bore provided in the screw cap 36 into the chamber enclosed by the piece of tubing 34 and the screw cap 36.

If the spatula 14 is swung up out of the rest position shown in FIG. 1 into the operational position shown in FIG. 2, the surface of the spatula 14 on which the bunch 16 of light-conducting fibers emerges presses the contact sleeve 30, and with it the incandescent lamp 32, down against the force of the spring 38 until the base contact 42 on the incandescent lamp 32 touches the contact pin 28 of the battery unit. This switches on the incandescent lamp 32. If the spatula 14 is folded down again into the rest position shown in FIG. 1, then the spring 38 presses the incandescent lamp 32 with the contact sleeve 30 upwards so that the incandescent lamp 32 is switched off again.

In this embodiment the contact sleeve 30 can be drawn out of the attachment 24 on the handle 10 by gripping the flange 31 and overcoming the restraining effect of the locking device. The incandescent lamp 32 then simply falls out of the contact sleeve 30 and can be changed. Replacement of the incandescent lamp 32 with the contact sleeve 30 in the attachment 24 is carried out in the reverse manner, by pressure on the flange 31 until the locking device is overcome.

In the embodiment shown in FIGS. 3 and 4 a bore is formed in the external end face of the attachment 24 to take a sliding sleeve, on the upper end of which there is a rim 46 and on the outer surface of which there is a collar 48. The sliding sleeve 44 can be moved in the axial direction between the limits set by the rim 46 and the collar 48.

In this construction form the contact sleeve 30 bearing the incandescent lamp 32 is mounted movably in the upper end of the battery unit 26. On the lower end of the contact sleeve 30 there is a flange 50 which ensures that the contact sleeve 30 does not fall out. The spring 38 which presses up the contact sleeve 30 and the incandescent lamp 32 screwed into it is braced between the contact sleeve 30 and a surface surrounding the contact pin 28 of the battery unit 26.

When the spatula 14 is swung up into the operational position shown in FIG. 4, the sliding sleeve 44 is pressed downwards by the surface of the spatula 14 which comes into contact with it. The sliding sleeve 44 presses in turn on the contact sleeve 30 and the incandescent lamp 32, so that the base contact 42 comes into contact with the contact pin 28 of the battery unit 26 and the incandescent lamp is switched on. Conversely, when the spatula 14 is folded down into the position shown in FIG. 3, the contact sleeve 30, the incandescent lamp 32 and the sliding sleeve 44 are pressed upwards so that the base contact 42 moves away from the contact pin 28 and the incandescent lamp 32 is switched off.

To change the incandescent lamp 32 the screw cap 22 is undone from the cylindrical housing 20 of the handle 10 and the battery unit 26, together with the contact sleeve 30 and the incandescent lamp 32, is taken out. Then the incandescent lamp 32 is screwed out of the contact sleeve 30 and replaced by a new one. The battery unit 26 with the new incandescent lamp 32 can now be reinserted in the handle 10. The appliance is thus ready for use again very quickly.

The embodiment shown in FIGS. 5 and 6 is like that shown in FIGS. 3 and 4 insofar as the incandescent lamp 32 is again connected to the battery unit 26. However, it is not mounted movably in the battery unit, but directly in the central bore of a cap 52 which encircles the contact pin 28 of the battery unit 26. In this instance the incandescent lamp 32 projects into a central bore provided in the attachment 24. In addition to the central bore there is another bore running parallel to it, to house an actuating pin 54. A spring contact 58 is attached to the inner surface of the attachment 24 by means of a screw 56 and is loaded by the actuating pin 54.

When the spatula 14 is swung up into the operational position shown in FIG. 6 the actuating pin 54 is pressed downwards by the surface surrounding the light inlet surface of the bunch 16 of light-conducting fibers, so that in turn this presses down the spring contact 58 until this comes into contact with the socket of the incandescent lamp 32, thus switching on the incandescent lamp. If the spatula 14 is folded down into the rest position shown in FIG. 5, the spring contact 58 is lifted off the socket of the incandescent lamp 32, so the incandescent lamp 32 is switched off again. The actuating pin 54 is again pressed upwards by the spring contact 58. To change the incandescent lamp 32, the same procedure is carried out as for the construction example shown in FIGS. 3 and 4.

The attachment 24 can have the same shape in both the embodiments shown in FIGS. 3 and 4, and FIGS. 5 and 6. For the embodiment shown in FIGS. 3 and 4 the sliding sleeve 44 will be inserted in the central bore in the attachment 24, while for the embodiment shown in FIGS. 5 and 6 the sliding sleeve 44 will be omitted, the spring contact 58 will be fixed to the attachment with the aid of the screw 56, and the actuating pin 54 will be inserted in the bore provided for this purpose.

What is claimed is:

1. A laryngoscope comprising a handle, a lamp mounted within one end of said handle, said lamp being movable between an energized position and a de-energized position, said lamp being electrically connected to power supply terminals within said handle when in said energized position and being disconnected from at least one of said power supply terminals when in said de-energized position, a spatula pivotally mounted on said handle adjacent said lamp, said spatula being movable between a non-operating position and an operating position, means for moving said lamp into said energized position when said spatula is moved to said operating position and for moving said lamp to said de-energized position when said spatula is moved to said non-operating position so as to energize said lamp, light transmissive means associated with said spatula for conducting light from said lamp to the field under observation, and means for supporting said lamp in said handle and movable therewith, said supporting means having a protruding part engageable from outside said one end of said handle, said one end of said handle and said supporting means constructed and arranged so that said supporting means can be removed from said handle in a direction away from said operating position by engagement of said protruding part for replacement of said lamp therein when said spatula is moved from said operating position.

2. The laryngoscope as set forth in claim 1 wherein said light transmissive means comprises a bundle of optical fibers extending from the proximate end of said spatula to a distal area along said spatula to illuminate the field of view.

3. The laryngoscope as set forth in claim 1 wherein said handle includes an attachment mounted at said one end of said handle, said attachment having a central bore therethrough and an enclosure extending from one end of said attachment into said handle in alignment with said bore.

4. The laryngoscope as set forth in claim 3 wherein said supporting means movably supports said lamp within said bore for movement of said lamp to and from said energized position where said lamp makes electrical contact with a power supply terminal extending into a portion of said enclosure.

5. The laryngoscope as set forth in claim 1 wherein said supporting means includes at one end means for retaining said lamp therein.

6. The laryngoscope as set forth in claim 5 further including means for holding one end of said lamp against said retaining means by pressing against the other end of said lamp.

7. The laryngoscope as set forth in claim 1 wherein said protruding part projects beyond said one end of said handle and defines a flange which facilitates the manual removal of said supporting means from said handle and said lamp therewith.

8. A laryngoscope comprising, a handle including an attachment mounted at one end of said handle, said attachment having a bore therethrough and an enclosure extending from one end of said attachment into said handle in alignment with said bore, a lamp mounted within said bore, said lamp being movable between an energized position and a de-energized position, said lamp being electrically connected to power supply terminals within said handle when in said energized position and being disconnected from at least one of said power supply terminals when in said de-energized position, a spatula pivotally mounted on said handle in the vicinity of said attachment adjacent said lamp, said spatula being movable between a non-operating position and an operating position, means for moving said lamp into said energized position when said spatula is moved to said operating position and for moving said lamp to said de-energized position when said spatula is moved to said non-operating position so as to energize said lamp, light transmissive means associated with said spatula for conducting light from said lamp to the field under observation, and means for supporting said lamp in said bore and movable therewith, said supporting means having at one end means for retaining said lamp therein and a protruding part engageable from outside said handle at the other end of said attachment, said attachment and said supporting means constructed and arranged so that said supporting means can be removed from said bore in a direction away from said enclosure by engagement of said protruding part for replacement of said lamp therein when said spatula is moved from said operating position.

9. The laryngoscope as set forth in claim 8 further including means within said enclosure for holding one end of said lamp against said retaining means by pressing against the other end of said lamp.

10. The laryngoscope as set forth in claim 9 wherein said holding means includes a spring in contact with one end of said enclosure and in contact with a ring member encircling said other end of said lamp.

11. The laryngoscope as set forth in claim 9 wherein the movement of said spatula to said operating position causes movement of said lamp to and from said energized position against said holding means such that said other end of said lamp makes electrical contact with a power supply terminal extending into a portion of said enclosure.

12. The laryngoscope as set forth in claim 8 wherein said enclosure comprises a tube extending from said one end of said attachment into said handle and having a removable cap closing one end of said tube.

* * * * *